(12) United States Patent
Breitweiser (10) Patent No.: US 7,850,650 B2
(45) Date of Patent: Dec. 14, 2010

(54) NEEDLE SAFETY SHIELD WITH RESET

(75) Inventor: Kenneth M. Breitweiser, Brighton, IL (US)

(73) Assignee: Covidien AG (CH)

( * ) Notice: Subject to any disclaimer, the term of this patent is extended or adjusted under 35 U.S.C. 154(b) by 1517 days.

(21) Appl. No.: 11/179,696

(22) Filed: Jul. 11, 2005

(65) Prior Publication Data

US 2007/0016139 A1    Jan. 18, 2007

(51) Int. Cl.
*A61M 5/32* (2006.01)
(52) U.S. Cl. .................................. 604/162; 604/110
(58) Field of Classification Search ............... 604/110, 604/162, 164.08, 192, 164.01, 198
See application file for complete search history.

(56) References Cited

U.S. PATENT DOCUMENTS

| | | |
|---|---|---|
| 1,115,561 A | 11/1914 | Northey |
| 1,436,707 A | 11/1922 | Gaschke |
| 1,518,531 A | 12/1924 | Lung |
| 2,219,605 A | 6/1938 | Turkel |
| 2,854,976 A | 10/1958 | Heydrich |
| 3,254,533 A | 6/1966 | Tongret |
| 3,539,034 A | 11/1970 | Tafeen |
| 3,610,240 A | 10/1971 | Harautuneian |
| 3,681,991 A | 8/1972 | Eberly |
| 3,729,998 A | 5/1973 | Mueller et al. |
| 3,822,598 A | 7/1974 | Hunter et al. |
| 3,884,230 A | 5/1975 | Wulff |
| 3,890,971 A | 6/1975 | Leeson et al. |
| 3,893,058 A | 7/1975 | Keith |
| 3,893,445 A | 7/1975 | Hofsess |
| 3,904,033 A | 9/1975 | Haerr |
| 3,915,003 A | 10/1975 | Adams |
| 3,946,613 A | 3/1976 | Silver |
| 3,976,070 A | 8/1976 | Dumont |
| 4,008,614 A | 2/1977 | Turner et al. |
| 4,010,737 A | 3/1977 | Vilaghy et al. |
| 4,026,287 A | 5/1977 | Haller |
| 4,099,518 A | 7/1978 | Baylis et al. |

(Continued)

FOREIGN PATENT DOCUMENTS

DE      3805567      8/1989

(Continued)

OTHER PUBLICATIONS

Office action dated Feb. 3, 2010 from related U.S. Appl. No. 11/179,090, 5 pgs.

(Continued)

*Primary Examiner*—Nicholas D Lucchesi
*Assistant Examiner*—Laura A Bouchelle
(74) *Attorney, Agent, or Firm*—Lisa E. Winsor, Esq.

(57) ABSTRACT

A safety shield is capable of being moved on a needle assembly to cover a sharp tip of the needle assembly. The shield can be locked in place over the sharp tip by a locking mechanism. The safety shield has a locking mechanism for locking the shield in place covering the sharp needle tip. The safety shield also has an unlocking mechanism that can move to release the locking mechanism and allow the shield to be moved to uncover the sharp tip. A reset member may include projecting portions that can be received through the shield to actuate the unlocking mechanism for releasing the locking mechanism.

6 Claims, 8 Drawing Sheets

U.S. PATENT DOCUMENTS

| | | |
|---|---|---|
| D249,475 S | 9/1978 | Turner et al. |
| 4,112,762 A | 9/1978 | Turner et al. |
| 4,139,009 A | 2/1979 | Alvarez |
| 4,142,517 A | 3/1979 | Stavropoulos et al. |
| 4,143,853 A | 3/1979 | Abramson |
| 4,160,450 A | 7/1979 | Doherty |
| 4,163,446 A | 8/1979 | Jamshidi |
| 4,177,797 A | 12/1979 | Baylis et al. |
| 4,183,248 A | 1/1980 | West |
| D255,997 S | 7/1980 | Maeda |
| 4,211,214 A | 7/1980 | Chikashige |
| 4,256,119 A | 3/1981 | Gauthier |
| 4,258,713 A | 3/1981 | Wardlaw |
| 4,258,722 A | 3/1981 | Sessions et al. |
| 4,262,676 A | 4/1981 | Jamshidi |
| 4,266,543 A | 5/1981 | Blum |
| 4,266,555 A | 5/1981 | Jamshidi |
| 4,314,565 A | 2/1982 | Lee |
| 4,356,828 A | 11/1982 | Jamshidi |
| 4,392,859 A | 7/1983 | Dent |
| 4,403,617 A | 9/1983 | Tretinyak |
| 4,425,120 A | 1/1984 | Sampson et al. |
| 4,438,884 A | 3/1984 | O'Brien et al. |
| 4,469,109 A | 9/1984 | Mehl |
| 4,482,348 A | 11/1984 | Dent |
| 4,487,209 A | 12/1984 | Mehl |
| 4,513,754 A | 4/1985 | Lee |
| 4,543,966 A | 10/1985 | Islam et al. |
| 4,572,365 A | 2/1986 | Bruno et al. |
| 4,573,976 A | 3/1986 | Sampson et al. |
| 4,613,329 A | 9/1986 | Bodicky |
| 4,619,271 A | 10/1986 | Burger et al. |
| 4,630,616 A | 12/1986 | Tretinyak |
| 4,631,057 A | 12/1986 | Mitchell |
| 4,639,249 A | 1/1987 | Larson |
| 4,642,785 A | 2/1987 | Packard et al. |
| 4,643,199 A | 2/1987 | Jennings |
| 4,643,200 A | 2/1987 | Jennings |
| 4,655,226 A | 4/1987 | Lee |
| 4,664,654 A | 5/1987 | Strauss |
| 4,676,783 A | 6/1987 | Jagger et al. |
| 4,681,567 A | 7/1987 | Masters |
| 4,693,708 A | 9/1987 | Wanderer |
| 4,695,274 A | 9/1987 | Fox |
| D292,493 S | 10/1987 | King |
| D292,494 S | 10/1987 | King |
| D293,215 S | 12/1987 | Bruno et al. |
| 4,723,943 A | 2/1988 | Spencer |
| 4,725,267 A | 2/1988 | Vaillancourt |
| 4,728,320 A | 3/1988 | Chen |
| 4,735,619 A | 4/1988 | Sperry |
| 4,737,144 A | 4/1988 | Choksi |
| 4,738,663 A | 4/1988 | Bogan |
| 4,741,627 A | 5/1988 | Fukui |
| 4,743,233 A | 5/1988 | Schneider |
| 4,747,831 A | 5/1988 | Kulli |
| 4,747,836 A | 5/1988 | Luther |
| 4,747,837 A | 5/1988 | Hauck |
| 4,752,290 A | 6/1988 | Schramm |
| 4,762,516 A | 8/1988 | Luther |
| 4,770,655 A | 9/1988 | Haber et al. |
| 4,772,272 A | 9/1988 | McFarland |
| 4,775,363 A | 10/1988 | Sandsdalen |
| 4,781,684 A | 11/1988 | Trenner |
| 4,781,692 A | 11/1988 | Jagger et al. |
| 4,785,826 A | 11/1988 | Ward |
| 4,790,329 A | 12/1988 | Simon |
| 4,790,827 A | 12/1988 | Haber et al. |
| 4,790,828 A | 12/1988 | Dombrowski |
| 4,793,363 A | 12/1988 | Ausherman et al. |
| 4,795,432 A | 1/1989 | Karczmer |
| 4,804,371 A | 2/1989 | Vaillancourt |
| 4,804,372 A | 2/1989 | Laico |
| 4,810,248 A | 3/1989 | Masters |
| 4,813,426 A | 3/1989 | Haber et al. |
| 4,816,022 A | 3/1989 | Poncy |
| D300,728 S | 4/1989 | Ross |
| 4,819,659 A | 4/1989 | Sitar |
| 4,820,275 A | 4/1989 | Haber et al. |
| 4,826,488 A | 5/1989 | Nelson |
| 4,826,490 A | 5/1989 | Byrne et al. |
| 4,826,491 A | 5/1989 | Schramm |
| 4,834,718 A | 5/1989 | McDonald |
| 4,838,280 A | 6/1989 | Haaga |
| 4,838,282 A | 6/1989 | Strasser et al. |
| 4,842,586 A | 6/1989 | Hogan |
| 4,846,809 A | 7/1989 | Sims |
| 4,900,307 A | 2/1990 | Kulli |
| 4,904,242 A | 2/1990 | Kulli |
| 4,906,235 A | 3/1990 | Roberts |
| 4,909,793 A | 3/1990 | Vining |
| 4,911,694 A | 3/1990 | Dolan |
| 4,911,706 A | 3/1990 | Levitt |
| 4,915,702 A | 4/1990 | Haber |
| D307,558 S | 5/1990 | Messina et al. |
| 4,922,602 A | 5/1990 | Mehl |
| 4,927,414 A | 5/1990 | Kulli |
| 4,929,241 A | 5/1990 | Kulli |
| 4,931,044 A | 6/1990 | Beiter |
| 4,935,013 A | 6/1990 | Haber et al. |
| 4,943,283 A | 7/1990 | Hogan |
| 4,944,725 A | 7/1990 | McDonald |
| 4,950,250 A | 8/1990 | Haber |
| 4,952,207 A | 8/1990 | Lemieux |
| 4,955,866 A | 9/1990 | Corey |
| 4,958,625 A | 9/1990 | Bates et al. |
| 4,960,412 A | 10/1990 | Fink |
| 4,964,854 A | 10/1990 | Luther |
| 4,966,587 A | 10/1990 | Baumgart |
| 4,969,554 A | 11/1990 | Sawaya |
| 4,978,344 A | 12/1990 | Dombrowski |
| 4,986,279 A | 1/1991 | O'Neill |
| 4,994,041 A | 2/1991 | Dombrowski |
| 5,005,585 A | 4/1991 | Mazza |
| 5,012,818 A | 5/1991 | Joishy |
| 5,013,304 A | 5/1991 | Russell et al. |
| 5,031,634 A | 7/1991 | Simon |
| 5,036,860 A | 8/1991 | Leigh et al. |
| 5,047,044 A | 9/1991 | Smith et al. |
| 5,049,136 A | 9/1991 | Johnson |
| 5,051,109 A | 9/1991 | Simon |
| 5,053,017 A | 10/1991 | Chamuel |
| 5,057,085 A | 10/1991 | Kopans |
| 5,059,180 A | 10/1991 | McLees |
| 5,085,648 A | 2/1992 | Purdy et al. |
| 5,092,851 A | 3/1992 | Ragner |
| 5,102,394 A | 4/1992 | Lasaitis |
| 5,108,374 A | 4/1992 | Lemieux |
| 5,126,090 A | 6/1992 | Egolf et al. |
| 5,127,916 A | 7/1992 | Spencer et al. |
| 5,133,727 A | 7/1992 | Bales et al. |
| 5,135,504 A | 8/1992 | McLees |
| 5,147,327 A | 9/1992 | Johnson |
| 5,154,703 A | 10/1992 | Bonaldo |
| 5,171,229 A | 12/1992 | McNeil et al. |
| 5,172,702 A | 12/1992 | Leigh et al. |
| 5,176,256 A | 1/1993 | Sawaya |
| 5,183,468 A | 2/1993 | McLees |
| 5,195,533 A | 3/1993 | Chin et al. |
| 5,195,985 A | 3/1993 | Hall |
| 5,213,115 A | 5/1993 | Zytkovicz et al. |
| 5,215,525 A | 6/1993 | Sturman |
| 5,215,528 A | 6/1993 | Purdy et al. |
| 5,215,533 A | 6/1993 | Robb |

| | | | | | | |
|---|---|---|---|---|---|---|
| 5,217,438 A | 6/1993 | Davis | | 5,514,152 A | 5/1996 | Smith |
| 5,228,451 A | 7/1993 | Bales et al. | | 5,522,398 A | 6/1996 | Goldenberg et al. |
| 5,257,632 A | 11/1993 | Turkel et al. | | 5,526,821 A | 6/1996 | Jamshidi |
| 5,279,306 A | 1/1994 | Mehl | | 5,533,516 A | 7/1996 | Sahatjian |
| 5,279,563 A | 1/1994 | Brucker et al. | | 5,533,974 A | 7/1996 | Gaba |
| 5,279,591 A | 1/1994 | Simon | | 5,538,009 A | 7/1996 | Byrne et al. |
| 5,282,477 A | 2/1994 | Bauer | | 5,542,927 A | 8/1996 | Thome et al. |
| 5,295,977 A | 3/1994 | Cohen et al. | | 5,549,565 A | 8/1996 | Ryan et al. |
| 5,304,136 A | 4/1994 | Erskine | | 5,549,708 A | 8/1996 | Thome et al. |
| 5,312,359 A | 5/1994 | Wallace | | 5,553,624 A | 9/1996 | Francese et al. |
| 5,314,406 A | 5/1994 | Arias et al. | | 5,558,651 A | 9/1996 | Crawford et al. |
| 5,316,013 A | 5/1994 | Striebel, II et al. | | 5,562,629 A | 10/1996 | Haughton |
| 5,320,635 A | 6/1994 | Smith | | 5,562,633 A | 10/1996 | Wozencroft |
| 5,322,517 A | 6/1994 | Sircom et al. | | 5,562,683 A | 10/1996 | Chan |
| 5,324,288 A | 6/1994 | Billings et al. | | 5,569,217 A | 10/1996 | Luther |
| 5,328,482 A | 7/1994 | Sircom et al. | | 5,569,299 A | 10/1996 | Dill et al. |
| 5,331,971 A | 7/1994 | Bales et al. | | 5,570,783 A | 11/1996 | Thome et al. |
| 5,331,972 A | 7/1994 | Wadhwani et al. | | 5,573,008 A | 11/1996 | Robinson et al. |
| 5,334,158 A | 8/1994 | McLees | | 5,573,510 A | 11/1996 | Isaacson |
| 5,338,311 A | 8/1994 | Mahurkar | | 5,578,015 A | 11/1996 | Robb |
| 5,338,314 A | 8/1994 | Ryan | | 5,584,809 A | 12/1996 | Gaba |
| 5,341,816 A | 8/1994 | Allen | | 5,584,810 A | 12/1996 | Brimhall |
| 5,344,408 A | 9/1994 | Partika | | 5,584,818 A | 12/1996 | Morrison |
| 5,348,022 A | 9/1994 | Leigh et al. | | 5,586,990 A | 12/1996 | Hahnen et al. |
| 5,348,544 A | 9/1994 | Sweeney et al. | | 5,591,202 A | 1/1997 | Slater et al. |
| 5,356,421 A | 10/1994 | Castro | | 5,595,186 A | 1/1997 | Rubinstein et al. |
| 5,357,974 A | 10/1994 | Baldridge | | 5,599,310 A | 2/1997 | Bogert |
| 5,368,045 A | 11/1994 | Clement et al. | | 5,601,536 A | 2/1997 | Crawford et al. |
| 5,368,046 A | 11/1994 | Scarfone et al. | | 5,601,585 A | 2/1997 | Banik et al. |
| 5,370,623 A | 12/1994 | Kreamer | | 5,601,599 A | 2/1997 | Nunez |
| D354,921 S | 1/1995 | Narayanan | | 5,611,781 A | 3/1997 | Sircom et al. |
| 5,385,151 A | 1/1995 | Scarfone et al. | | 5,615,690 A | 4/1997 | Giurtino et al. |
| 5,385,570 A | 1/1995 | Chin et al. | | 5,616,135 A | 4/1997 | Thorne et al. |
| 5,389,104 A | 2/1995 | Hahnen et al. | | 5,623,969 A | 4/1997 | Raines |
| 5,389,106 A | 2/1995 | Tower | | 5,624,459 A | 4/1997 | Kortenbach et al. |
| 5,394,885 A | 3/1995 | Francese | | 5,630,506 A | 5/1997 | Thorne et al. |
| 5,395,375 A | 3/1995 | Turkel et al. | | 5,630,837 A | 5/1997 | Crowley |
| 5,396,900 A | 3/1995 | Slater et al. | | 5,632,555 A | 5/1997 | Gregory |
| 5,399,167 A | 3/1995 | Deniega | | 5,634,473 A | 6/1997 | Goldenberg et al. |
| 5,403,283 A | 4/1995 | Luther | | 5,643,307 A | 7/1997 | Turkel et al. |
| 5,405,323 A | 4/1995 | Rogers et al. | | 5,656,031 A | 8/1997 | Thorne et al. |
| 5,405,388 A | 4/1995 | Fox | | 5,662,610 A | 9/1997 | Sircom |
| 5,409,461 A | 4/1995 | Steinman | | 5,666,965 A | 9/1997 | Bales et al. |
| 5,411,486 A | 5/1995 | Zadini | | 5,669,883 A | 9/1997 | Scarfone et al. |
| 5,415,182 A | 5/1995 | Chin et al. | | 5,672,161 A | 9/1997 | Allen |
| 5,417,659 A | 5/1995 | Gaba | | 5,679,907 A | 10/1997 | Ruck |
| 5,417,709 A | 5/1995 | Slaterq | | 5,685,852 A | 11/1997 | Turkel et al. |
| 5,419,766 A | 5/1995 | Chang et al. | | 5,685,862 A | 11/1997 | Mahurkar |
| 5,421,522 A | 6/1995 | Bowen | | 5,687,907 A | 11/1997 | Holden |
| 5,423,766 A | 6/1995 | Di Cesare | | 5,690,619 A | 11/1997 | Erskine |
| 5,425,718 A | 6/1995 | Tay | | 5,693,022 A | 12/1997 | Haynes |
| 5,425,884 A | 6/1995 | Botz | | 5,693,031 A | 12/1997 | Ryan et al. |
| 5,429,138 A | 7/1995 | Jamshidi | | 5,695,467 A | 12/1997 | Miyata et al. |
| 5,429,616 A | 7/1995 | Schaffer | | 5,695,521 A | 12/1997 | Anderhub |
| 5,454,378 A | 10/1995 | Palmer et al. | | 5,697,904 A | 12/1997 | Raines et al. |
| 5,456,267 A | 10/1995 | Stark | | 5,697,907 A | 12/1997 | Gaba |
| 5,458,658 A | 10/1995 | Sircom | | 5,700,249 A | 12/1997 | Jenkins |
| 5,462,062 A | 10/1995 | Rubinstein et al. | | 5,700,250 A | 12/1997 | Erskine |
| 5,466,223 A | 11/1995 | Bressler et al. | | 5,702,080 A | 12/1997 | Whittier et al. |
| 5,471,992 A | 12/1995 | Banik et al. | | 5,702,369 A | 12/1997 | Mercereau |
| 5,473,629 A | 12/1995 | Muramoto | | 5,706,824 A | 1/1998 | Whitlier |
| 5,476,099 A | 12/1995 | Robinson et al. | | 5,707,392 A | 1/1998 | Kortenbach |
| 5,476,102 A | 12/1995 | Como et al. | | 5,713,368 A | 2/1998 | Leigh |
| 5,478,313 A | 12/1995 | White | | 5,713,888 A | 2/1998 | Neuenfeldt et al. |
| 5,480,385 A | 1/1996 | Thome et al. | | 5,715,832 A | 2/1998 | Kobhsh et al. |
| 5,482,054 A | 1/1996 | Slater et al. | | 5,718,688 A | 2/1998 | Wozencroft |
| 5,487,734 A | 1/1996 | Thome et al. | | 5,722,422 A | 3/1998 | Palmer et al. |
| 5,492,532 A | 2/1996 | Ryan et al. | | 5,730,150 A | 3/1998 | Peppel et al. |
| 5,501,675 A | 3/1996 | Erskine | | 5,730,724 A | 3/1998 | Plishka et al. |
| 5,507,296 A | 4/1996 | Bales et al. | | 5,735,827 A | 4/1998 | Adwers |
| 5,507,297 A | 4/1996 | Slater et al. | | 5,738,660 A | 4/1998 | Luther |
| 5,507,298 A | 4/1996 | Schramm et al. | | 5,738,665 A | 4/1998 | Caizza |
| 5,514,100 A | 5/1996 | Mahurkar | | 5,746,753 A | 5/1998 | Sullivan et al. |

| | | | | | | |
|---|---|---|---|---|---|---|
| 5,752,923 | A | 5/1998 | Terwilliger | 6,033,369 A | 3/2000 | Goldenberg |
| D395,609 | S | 6/1998 | Knieriem et al. | 6,036,361 A | 3/2000 | Gregory et al. |
| 5,758,655 | A | 6/1998 | Como Rodriguez et al. | 6,036,675 A | 3/2000 | Thorne et al. |
| 5,776,157 | A | 7/1998 | Thome et al. | 6,047,729 A | 4/2000 | Hollister et al. |
| 5,795,336 | A | 8/1998 | Romano et al. | 6,050,954 A | 4/2000 | Mittermeier |
| 5,807,275 | A | 9/1998 | Jamshidi | 6,050,976 A | 4/2000 | Thorne et al. |
| 5,807,277 | A | 9/1998 | Swaim | 6,053,877 A | 4/2000 | Banik et al. |
| 5,810,744 | A | 9/1998 | Chu et al. | 6,063,037 A | 5/2000 | Mittermeier et al. |
| 5,817,069 | A | 10/1998 | Arnett | 6,063,040 A | 5/2000 | Owen et al. |
| 5,823,970 | A | 10/1998 | Terwilliger | 6,071,284 A | 6/2000 | Fox |
| 5,823,971 | A | 10/1998 | Robinson et al. | 6,080,115 A | 6/2000 | Rubinstein |
| 5,823,997 | A | 10/1998 | Thorne | 6,083,176 A | 7/2000 | Terwilliger |
| 5,824,002 | A | 10/1998 | Gentelia et al. | 6,083,202 A | 7/2000 | Smith |
| D400,806 | S | 11/1998 | Tillack | 6,086,563 A | 7/2000 | Moulton et al. |
| D400,808 | S | 11/1998 | Schwan | 6,090,078 A | 7/2000 | Erskine |
| 5,836,917 | A | 11/1998 | Thome et al. | 6,090,108 A | 7/2000 | McBrayer et al. |
| 5,836,921 | A | 11/1998 | Mahurkar | 6,095,967 A | 8/2000 | Black et al. |
| 5,840,044 | A | 11/1998 | Dassa et al. | 6,096,005 A | 8/2000 | Botich |
| 5,843,001 | A | 12/1998 | Goldenberg | 6,102,920 A | 8/2000 | Sullivan et al. |
| 5,848,692 | A | 12/1998 | Thome et al. | 6,106,484 A | 8/2000 | Terwilliger |
| 5,853,393 | A | 12/1998 | Bogert | 6,110,128 A | 8/2000 | Andelin et al. |
| 5,860,955 | A | 1/1999 | Wright et al. | 6,110,129 A | 8/2000 | Terwilliger |
| 5,865,806 | A | 2/1999 | Howell | 6,110,176 A | 8/2000 | Shapira |
| 5,871,453 | A | 2/1999 | Banik et al. | RE36,885 E | 9/2000 | Blecher et al. |
| 5,873,886 | A | 2/1999 | Larsen et al. | 6,117,108 A | 9/2000 | Woehr et al. |
| 5,879,332 | A | 3/1999 | Schwemberger et al. | 6,117,112 A | 9/2000 | Mahurkar |
| 5,879,337 | A | 3/1999 | Kuracina et al. | 6,117,115 A | 9/2000 | Hill et al. |
| 5,879,338 | A | 3/1999 | Mahurkar | 6,132,401 A | 10/2000 | Van Der Meyden |
| 5,882,337 | A | 3/1999 | Bogert et al. | 6,135,110 A | 10/2000 | Roy |
| 5,885,226 | A | 3/1999 | Rubinstein et al. | 6,142,956 A | 11/2000 | Kortenbach et al. |
| 5,891,105 | A | 4/1999 | Mahurkar | 6,142,957 A | 11/2000 | Diamond et al. |
| 5,893,845 | A | 4/1999 | Newby | 6,149,629 A | 11/2000 | Wilson et al. |
| 5,893,876 | A | 4/1999 | Turkel et al. | 6,171,284 B1 | 1/2001 | Kao |
| 5,895,361 | A | 4/1999 | Turturro | 6,174,292 B1 | 1/2001 | Kortenbach et al. |
| 5,897,507 | A | 4/1999 | Kortenbach et al. | 6,193,671 B1 | 2/2001 | Turturro et al. |
| 5,906,594 | A | 5/1999 | Scarfone et al. | 6,197,007 B1 | 3/2001 | Thome et al. |
| 5,910,130 | A | 6/1999 | Calzza et al. | 6,203,527 B1 | 3/2001 | Zadini |
| 5,910,132 | A | 6/1999 | Schultz | 6,210,373 B1 | 4/2001 | Allmon |
| 5,911,705 | A | 6/1999 | Howell | 6,217,556 B1 | 4/2001 | Ellingson et al. |
| 5,913,859 | A | 6/1999 | Shapira | 6,221,029 B1 | 4/2001 | Mathis et al. |
| 5,916,175 | A | 6/1999 | Bauer | 6,221,047 B1 | 4/2001 | Greene et al. |
| 5,928,162 | A | 7/1999 | Giurtino et al. | 6,224,569 B1 | 5/2001 | Brimhall |
| 5,928,163 | A | 7/1999 | Roberts et al. | 6,224,576 B1 | 5/2001 | Thome et al. |
| 5,928,200 | A | 7/1999 | Thorne et al. | 6,234,773 B1 | 5/2001 | Hill et al. |
| 5,935,109 | A | 8/1999 | Donnan | 6,254,575 B1 | 7/2001 | Thome, Jr. et al. |
| 5,947,930 | A | 9/1999 | Schwemberger et al. | 6,261,242 B1 | 7/2001 | Roberts et al. |
| 5,951,489 | A | 9/1999 | Bauer | 6,264,617 B1 | 7/2001 | Bales et al. |
| 5,951,525 | A | 9/1999 | Thorne et al. | D446,135 S | 8/2001 | Chen |
| 5,951,582 | A | 9/1999 | Thorne et al. | 6,280,399 B1 | 8/2001 | Rossin et al. |
| 5,954,696 | A | 9/1999 | Ryan | 6,280,401 B1 | 8/2001 | Mahurkar |
| 5,954,698 | A | 9/1999 | Pike | 6,280,419 B1 | 8/2001 | Vojtasek |
| 5,957,863 | A | 9/1999 | Koblish et al. | 6,280,420 B1 | 8/2001 | Ferguson et al. |
| 5,957,887 | A | 9/1999 | Osterlind et al. | D448,314 S | 9/2001 | Chen |
| 5,957,892 | A | 9/1999 | Thorne | 6,283,925 B1 | 9/2001 | Terwilliger |
| 5,961,526 | A | 10/1999 | Chu et al. | 6,287,278 B1 | 9/2001 | Woehr et al. |
| 5,961,534 | A | 10/1999 | Banik et al. | 6,293,700 B1 | 9/2001 | Lund et al. |
| 5,964,717 | A | 10/1999 | Gottlieb et al. | 6,302,852 B1 | 10/2001 | Fleming, III et al. |
| 5,967,490 | A | 10/1999 | Pike | 6,309,376 B1 | 10/2001 | Alesi |
| 5,976,115 | A | 11/1999 | Parris et al. | 6,312,394 B1 | 11/2001 | Fleming, III |
| 5,979,840 | A | 11/1999 | Hollister et al. | 6,315,737 B1 | 11/2001 | Skinner |
| 5,980,488 | A | 11/1999 | Thorne | 6,321,782 B1 | 11/2001 | Hollister |
| 5,989,196 | A | 11/1999 | Chu et al. | 6,322,537 B1 | 11/2001 | Chang |
| 5,989,229 | A | 11/1999 | Chiappetta | 6,328,701 B1 | 12/2001 | Terwilliger |
| 5,989,241 | A | 11/1999 | Plishka et al. | 6,328,713 B1 | 12/2001 | Hollister |
| 5,993,426 | A | 11/1999 | Hollister | 6,334,857 B1 | 1/2002 | Hollister et al. |
| 6,000,846 | A | 12/1999 | Gregory et al. | 6,336,915 B1 | 1/2002 | Scarfone et al. |
| 6,001,080 | A | 12/1999 | Kuracina et al. | 6,340,351 B1 | 1/2002 | Goldenberg |
| 6,004,294 | A | 12/1999 | Brimhall et al. | 6,358,252 B1 | 3/2002 | Shapira |
| 6,007,560 | A | 12/1999 | Gottlieb et al. | 6,358,265 B1 | 3/2002 | Thome, Jr. et al. |
| 6,015,391 | A | 1/2000 | Rishton et al. | 6,361,525 B2 | 3/2002 | Capes et al. |
| 6,022,324 | A | 2/2000 | Skinner | 6,379,333 B1 | 4/2002 | Brimhall et al. |
| 6,024,708 | A | 2/2000 | Bales et al. | 6,379,338 B1 | 4/2002 | Garvin |
| 6,024,727 | A | 2/2000 | Thorne et al. | 6,383,144 B1 | 5/2002 | Mooney |

| | | | | | | |
|---|---|---|---|---|---|---|
| 6,406,459 | B1 | 6/2002 | Allmon | 6,796,962 | B2 | 9/2004 | Ferguson et al. |
| 6,409,701 | B1 | 6/2002 | Cohn et al. | 6,798,348 | B1 | 9/2004 | Wilker et al. |
| 6,416,484 | B1 | 7/2002 | Miller et al. | 6,811,308 | B2 | 11/2004 | Chapman |
| 6,423,034 | B2 | 7/2002 | Scarfone et al. | 6,821,267 | B2 | 11/2004 | Veillon, Jr. et al. |
| 6,439,768 | B1 | 8/2002 | Wu et al. | 6,827,488 | B2 | 12/2004 | Knieriem et al. |
| 6,443,910 | B1 | 9/2002 | Krueger et al. | 6,832,990 | B2 | 12/2004 | Kortenbach et al. |
| 6,443,927 | B1 | 9/2002 | Cook | 6,832,992 | B2 | 12/2004 | Wilkinson |
| 6,443,929 | B1 | 9/2002 | Kuracina et al. | 6,839,651 | B2 | 1/2005 | Lantz et al. |
| 6,478,751 | B1 | 11/2002 | Krueger et al. | 6,846,314 | B2 | 1/2005 | Shapira |
| 6,485,468 | B2 | 11/2002 | Vojtasek | 6,849,051 | B2 | 2/2005 | Sramek et al. |
| 6,485,473 | B1 | 11/2002 | Lynn | 6,855,128 | B2 | 2/2005 | Swenson |
| 6,488,663 | B1 | 12/2002 | Steg | 6,855,130 | B2 | 2/2005 | Saulenas et al. |
| 6,500,129 | B1 | 12/2002 | Mahurkar | 6,860,871 | B2 | 3/2005 | Kuracina et al. |
| 6,501,384 | B2 | 12/2002 | Chapman | 6,875,183 | B2 | 4/2005 | Cervi |
| 6,517,516 | B1 | 2/2003 | Caizza | 6,890,308 | B2 | 5/2005 | Islam |
| 6,519,569 | B1 | 2/2003 | White et al. | 6,902,546 | B2 | 6/2005 | Ferguson |
| 6,520,938 | B1 | 2/2003 | Funderburk | 6,916,292 | B2 | 7/2005 | Morawski et al. |
| 6,537,255 | B1 | 3/2003 | Raines | 6,916,311 | B2 | 7/2005 | Vojtasek |
| 6,537,259 | B1 | 3/2003 | Niermann | 6,916,314 | B2 | 7/2005 | Schneider |
| 6,544,194 | B1 | 4/2003 | Korlenbach et al. | 6,923,813 | B2 | 8/2005 | Phillips et al. |
| 6,551,287 | B2 | 4/2003 | Hollister | 6,936,036 | B2 | 8/2005 | Wilkinson |
| 6,551,328 | B2 | 4/2003 | Kortenbach | D512,506 | S | 12/2005 | Layne et al. |
| 6,554,778 | B1 | 4/2003 | Fleming, III | D512,924 | S | 12/2005 | Ikeda |
| 6,569,125 | B2 | 5/2003 | Jepson et al. | 6,976,783 | B2 | 12/2005 | Chen |
| 6,575,919 | B1 | 6/2003 | Feiley et al. | 6,981,948 | B2 | 1/2006 | Pellegrino et al. |
| 6,582,402 | B1 | 6/2003 | Erskine | 6,984,213 | B2 | 1/2006 | Homer et al. |
| 6,582,446 | B1 | 6/2003 | Marchosky | 6,989,003 | B2 | 1/2006 | Wing et al. |
| 6,585,704 | B2 | 7/2003 | Luther et al. | 7,008,402 | B2 | 3/2006 | Ferguson et al. |
| 6,592,556 | B1 | 7/2003 | Thome | 7,018,343 | B2 | 3/2006 | Plishka |
| 6,595,954 | B1 | 7/2003 | Luther | 7,021,824 | B2 | 4/2006 | Wawro et al. |
| 6,595,955 | B2 | 7/2003 | Ferguson et al. | 7,033,324 | B2 | 4/2006 | Giusti et al. |
| 6,613,018 | B2 | 9/2003 | Bagga et al. | 7,036,984 | B2 | 5/2006 | Penney et al. |
| 6,616,604 | B1 | 9/2003 | Bass et al. | 7,063,703 | B2 | 6/2006 | Reo |
| 6,616,630 | B1 | 9/2003 | Woehr et al. | 7,112,191 | B2 | 9/2006 | Daga |
| 6,623,458 | B2 | 9/2003 | Woehr et al. | 7,118,552 | B2 | 10/2006 | Shaw |
| 6,626,850 | B1 | 9/2003 | Chau et al. | 7,207,973 | B2 | 4/2007 | Barrelle |
| D480,977 | S | 10/2003 | Wawro et al. | 7,214,208 | B2 | 5/2007 | Vaillancourt |
| D481,321 | S | 10/2003 | Knieriem et al. | 7,226,434 | B2 | 6/2007 | Carlyon et al. |
| 6,629,959 | B2 | 10/2003 | Kuracina et al. | 7,238,169 | B2 | 7/2007 | Takagi et al. |
| 6,634,789 | B2 | 10/2003 | Babkes | 7,247,148 | B2 | 7/2007 | Murashita |
| 6,635,033 | B1 | 10/2003 | Hill et al. | 7,255,475 | B2 | 8/2007 | Quinn et al. |
| 6,638,252 | B2 | 10/2003 | Moulton | 7,264,613 | B2 | 9/2007 | Woehr et al. |
| 6,638,254 | B2 | 10/2003 | Nakagami | 7,300,420 | B2 | 11/2007 | Doyle |
| 6,641,562 | B1 | 11/2003 | Peterson | 7,303,548 | B2 | 12/2007 | Rhad et al. |
| 6,652,486 | B2 | 11/2003 | Bialecki et al. | 7,316,507 | B2 | 1/2008 | Sisk et al. |
| 6,652,490 | B2 | 11/2003 | Howell | 7,357,784 | B2 | 4/2008 | Ferguson |
| 6,663,592 | B2 | 12/2003 | Rhad et al. | 7,377,908 | B2 | 5/2008 | Buetikofer et al. |
| 6,673,047 | B2 | 1/2004 | Crawford | 7,488,306 | B2 | 2/2009 | Nguyen |
| 6,673,060 | B1 | 1/2004 | Fleming, III | 7,500,965 | B2 | 3/2009 | Menzi et al. |
| 6,682,510 | B2 | 1/2004 | Niermann | 7,513,888 | B2 | 4/2009 | Sircom |
| 6,689,102 | B2 | 2/2004 | Greene | 2001/0021827 | | 9/2001 | Ferguson et al. |
| 6,692,471 | B2 | 2/2004 | Boudreaux | 2002/0021827 | A1 | 2/2002 | Smith |
| 6,695,814 | B2 | 2/2004 | Greene et al. | 2003/0002562 | A1 | 1/2003 | Yerlikaya et al. |
| 6,698,921 | B2 | 3/2004 | Siefert | 2003/0100868 | A1 | 5/2003 | Ferguson et al. |
| 6,699,221 | B2 | 3/2004 | Vaillancourt | 2003/0114797 | A1 | 6/2003 | Vaillancourt et al. |
| 6,702,786 | B2 | 3/2004 | Olovson | 2003/0144627 | A1 | 7/2003 | Woehr et al. |
| 6,709,419 | B2 | 3/2004 | Woehr | 2003/0176810 | A1 | 9/2003 | Maahs et al. |
| 6,719,732 | B2 | 4/2004 | Courteix | 2003/0191438 | A1 | 10/2003 | Ferguson et al. |
| 6,723,075 | B2 | 4/2004 | Davey et al. | 2003/0220617 | A1 | 11/2003 | Dickerson |
| 6,727,805 | B2 | 4/2004 | Hollister et al. | 2004/0071182 | A1 | 4/2004 | Quinn et al. |
| 6,730,043 | B2 | 5/2004 | Krueger et al. | 2004/0077973 | A1 | 4/2004 | Groenke et al. |
| 6,731,216 | B2 | 5/2004 | Ho et al. | 2004/0078003 | A1 | 4/2004 | Smith et al. |
| 6,740,063 | B2 | 5/2004 | Lynn | 2004/0078007 | A1 | 4/2004 | Nguyen |
| 6,749,576 | B2 | 6/2004 | Bauer | 2004/0092889 | A1 | 5/2004 | Ferguson et al. |
| 6,749,588 | B1 | 6/2004 | Howell et al. | 2004/0133167 | A1 | 7/2004 | Ferguson et al. |
| 6,749,595 | B1 | 6/2004 | Murphy | 2004/0153005 | A1 | 8/2004 | Krueger |
| 6,755,793 | B2 | 6/2004 | Lamoureux et al. | 2004/0162526 | A1 | 8/2004 | Vaillancourt |
| 6,761,704 | B2 | 7/2004 | Crawford | 2004/0171989 | A1 | 9/2004 | Homer et al. |
| 6,761,706 | B2 | 7/2004 | Vaillancourt | 2004/0186434 | A1 | 9/2004 | Harding et al. |
| 6,764,567 | B2 | 7/2004 | Sperko et al. | 2004/0225260 | A1 | 11/2004 | Villa et al. |
| 6,767,336 | B1 | 7/2004 | Kaplan | 2004/0236288 | A1 | 11/2004 | Howell et al. |
| 6,770,050 | B2 | 8/2004 | Epstein | 2004/0236289 | A1 | 11/2004 | Ferguson et al. |
| 6,770,053 | B2 | 8/2004 | Scarfone et al. | 2005/0027263 | A1 | 2/2005 | Woehr et al. |

| | | |
|---|---|---|
| 2005/0043691 A1 | 2/2005 | Ferguson |
| 2005/0054987 A1 | 3/2005 | Perez et al. |
| 2005/0070850 A1 | 3/2005 | Albrecht |
| 2005/0070851 A1 | 3/2005 | Thompson et al. |
| 2005/0070855 A1 | 3/2005 | Ferguson et al. |
| 2005/0075609 A1 | 4/2005 | Latona |
| 2005/0090763 A1 | 4/2005 | Wang |
| 2005/0090764 A1 | 4/2005 | Wang |
| 2005/0113716 A1 | 5/2005 | Mueller, Jr. et al. |
| 2005/0119652 A1 | 6/2005 | Velter et al. |
| 2005/0131345 A1 | 6/2005 | Miller |
| 2005/0137500 A1 | 6/2005 | Wingler |
| 2005/0165404 A1 | 7/2005 | Miller |
| 2005/0192536 A1 | 9/2005 | Takagi et al. |
| 2005/0203459 A1 | 9/2005 | Alchas |
| 2005/0267383 A1 | 12/2005 | Groenke et al. |
| 2005/0273057 A1 | 12/2005 | Popov |
| 2005/0277845 A1 | 12/2005 | Cooke et al. |
| 2005/0288605 A1 | 12/2005 | Pellegrino et al. |
| 2006/0052721 A1 | 3/2006 | Dunker et al. |
| 2006/0064101 A1 | 3/2006 | Arramon |
| 2006/0116603 A1 | 6/2006 | Shibazaki et al. |
| 2006/0178625 A1 | 8/2006 | Lim et al. |
| 2006/0189934 A1 | 8/2006 | Kuracina et al. |
| 2006/0189936 A1 | 8/2006 | Carlyon et al. |
| 2006/0200195 A1 | 9/2006 | Yang |
| 2006/0276772 A1 | 12/2006 | Moos et al. |
| 2007/0110122 A1 | 5/2007 | Sisk et al. |
| 2007/0116089 A1 | 5/2007 | Bisch et al. |
| 2008/0097345 A1 | 4/2008 | Ferguson |
| 2008/0112461 A1 | 5/2008 | Bisch et al. |
| 2008/0294065 A1 | 11/2008 | Waldhoff et al. |

FOREIGN PATENT DOCUMENTS

| | | |
|---|---|---|
| DE | 3805567 A1 | 8/1989 |
| EP | 1 358 846 | 11/2003 |
| EP | 1358846 A1 | 11/2003 |
| JP | 6-241914 | 9/1994 |
| JP | 6-241914 A | 9/1994 |
| WO | 96-22800 A1 | 8/1996 |
| WO | 97-42989 A1 | 11/1997 |
| WO | WO 97-42989 | 11/1997 |
| WO | WO 2004/060138 | 7/2004 |
| WO | 2004091687 A2 | 10/2004 |
| WO | WO 2004/091687 | 10/2004 |
| WO | WO 2005/009246 | 2/2005 |
| WO | 2005053774 A1 | 6/2005 |
| WO | WO 2005/053774 | 6/2005 |
| WO | WO 2005053774 A1 * | 6/2005 |
| WO | WO 2005/060679 | 7/2005 |

OTHER PUBLICATIONS

Office action dated Feb. 4, 2010 from related U.S. Appl. No. 11/179,438, 7 pgs.

* cited by examiner

NEEDLE SAFETY SHIELD WITH RESET

BACKGROUND OF THE INVENTION

This invention relates generally to needle assemblies and more particularly to needle assemblies that have shields to cover sharp ends of needles.

Needle assemblies of the present invention have particular, although not exclusive application in the field of medicine and have needles with sharpened ends for use in piercing the skin to withdraw materials as needed. The needle is supported by some other structure that is used to manipulate the needle. The most common example is a syringe. However, some needle assemblies require the application of substantial force in use. One example of such a needle assembly is a bone marrow needle assembly that is used to penetrate cortical bone to reach the intramedullary canal for withdrawing liquid or a biopsy sample of bore marrow, or for infusing the canal with a selected material. Typically, the needle includes a cannula and a stylet that is received in the cannula and has a hard, sharp tip that can penetrate cortical bone. The tip projects out from the distal end of the cannula. The stylet can be withdrawn from the cannula after the needle penetrates the bone so that the hollow interior of the cannula can be used as a conduit for liquid or a receptacle to collect bone marrow.

In order to penetrate cortical bone, a substantial amount of force must be applied to the needle. For this reason, bone needle assemblies conventionally mount the needle in a handle that is sized and shaped so that the technician may comfortably grip the handle and apply the force necessary to penetrate the bone. The handle may comprise two handle members that can be selectively put together and separated for inserting the stylet into the cannula and removing the stylet from the cannula. A proximal handle member mounts the stylet and a distal handle member mounts the cannula. "Proximal" and "distal" refer to the relative location of the handle members to the technician when the needle assembly is in use. The proximal handle member is in contact with the palm of the technician's hand in use, and the distal handle member is on the opposite side of the proximal handle member from the palm.

Some needle assemblies, including bone needle assemblies, have associated safety mechanisms that shield the sharp tips of the needle components when they are not needed and after they have become contaminated with potentially hazardous biological material. The safety mechanism includes a shield and usually a mechanism for locking the shield in place over the sharpened tip. As a matter of convenience, and to enhance the probability that the safety feature will be used by a medical technician, the safety feature may be secured to the needle assembly. However, the safety feature must be retained out of the way when the needle assembly is being used, for example, to collect a liquid or solid sample from the intramedullary canal. The safety feature then must be released from its stowed position and moved to an operative position in which its shield covers the sharpened tip of the needle.

In cases where a sample (e.g., a bone marrow sample) is collected by the needle assembly, the sample has to be removed from the needle assembly. An obturator is a device including a long thin shaft, and in some cases includes a blunt tip, that can fit inside the cannula for pushing the sample of bone marrow out of the cannula. This can be done with the safety shield in position covering the sharp end of the cannula to protect the technician. In some cases it will be determined that the sample is not satisfactory and it will be necessary to obtain a second sample. It is not necessary to use a new needle assembly, because the needle assembly would be reused on the same patient. However, the shield is held in place over the tip of the needle assembly making it unusable for a collecting a second sample. Accordingly, there is a need for a needle assembly that can be easily reset for second use, but which will not result in inadvertent release of the safety shield.

SUMMARY OF THE INVENTION

In one aspect of the present invention, a needle assembly generally comprises mounting structure and a needle mounted on the mounting structure and extending outwardly therefrom. The needle has a longitudinal axis, a sharp end, and a central axial passageway. A safety shield associated with the needle comprises a tubular housing adapted for movement relative to the needle between a stowed position in which the tubular housing is spaced from the sharp end of the needle and a deployed position in which the tubular housing covers the sharp end. A locking mechanism is adapted to releasably lock the tubular housing in position covering the sharp end of the needle. An unlocking mechanism is adapted to engage the locking mechanism to unlock the tubular housing from the needle. An obturator includes a shaft sized and shaped for reception in the central axial passageway of the needle. A reset member operatively connects to the shaft and selectively engages the unlocking mechanism of the safety shield for moving the unlocking mechanism into selective engagement with the locking mechanism for releasing the locking mechanism to permit the tubular housing to move away from the sharp end of the needle.

In another aspect of the present invention, a resettable needle safety shield for use in selectively shielding and unshielding a sharp tip of a needle generally comprises a housing sized and shaped for substantially surrounding the sharp needle tip to hinder access to the sharp tip and a locking mechanism associated with the housing. The locking mechanism is adapted to lock the housing in position substantially surrounding the sharp needle tip. An unlocking mechanism is associated with the housing for movement relative to the housing between a first position in which the locking mechanism is free to lock the housing in position relative to the sharp needle tip and a second position in which the unlocking mechanism releases the locking mechanism to permit movement of the housing relative to the needle.

In yet another aspect of the present invention, a resettable needle safety shield for use in selectively shielding and unshielding a sharp tip of a needle generally comprises a housing sized and shaped for substantially surrounding the sharp needle tip to hinder access to the sharp tip and a locking mechanism associated with the housing. The locking mechanism is adapted to lock the housing in position substantially surrounding the sharp needle tip. The housing includes an end wall having at least one hole therein arranged in relation to the locking mechanism for receiving structure through the end wall for use in releasing the locking mechanism.

Other objects and features of the present invention will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
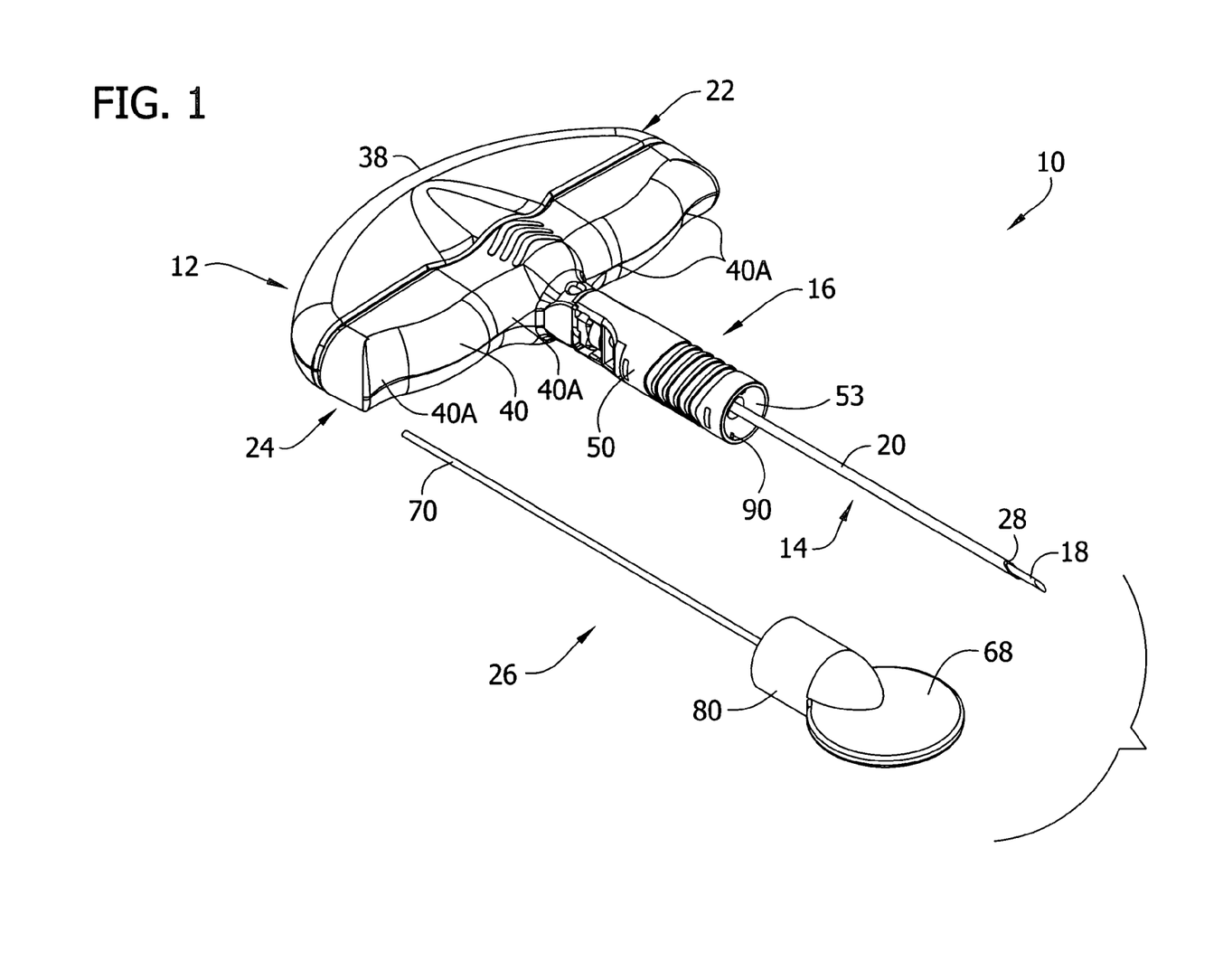
FIG. 1 is a perspective of a bone needle assembly including an obturator.

Referring now to the drawings and in particular to FIG. 1, a medical instrument constructed according to the principles of the present invention is shown in the form of a bone needle assembly, generally indicated at 10. The bone needle assembly includes a handle 12 (broadly, "mounting structure"), a needle 14 and a cannula safety shield 16, all reference numbers indicating their subjects generally. The needle 14 includes a stylet 18 and a cannula 20 that can receive the stylet. The handle 12 includes a first or proximal handle member (indicated generally at 22) mounting the stylet 18, and a second or distal handle member (indicated generally at 24) mounting the cannula 20. It will be understood that a needle could include only a single component part, or more than two parts within the scope of the present invention. Similarly, a handle could be a single part or more than two parts. The mounting structure for the needle 14 can be other than a handle without departing from the present invention. The needle assembly 10 further includes an obturator 26, which is described more fully below, that may be used to remove a sample captured in the cannula 20.

The cannula 20 has a central axial passage extending the length of the cannula and opening at both ends of the cannula. A distal tip 28 of the cannula 20 is beveled and sharpened. A proximal end portion of the cannula 20 is received in the distal handle member 24. The stylet 18 is solid and includes a sharp distal tip, and a proximal end portion of the stylet is received in the proximal handle member 22. The stylet 18 can be inserted through the axial passage opening in the proximal end portion of the cannula 20 and received entirely through the axial passage of the cannula so that its sharp distal tip projects axially outward from the distal tip 28 of the cannula. The stylet 18 provides the tool for penetrating the cortical bone, and can be removed from the cannula 20 once the intramedullary canal is accessed by the needle 14.

The handle 12 formed by the proximal and distal handle members 22, 24 has an ergonomic shape that can be comfortably received in a medical technician's hand, and allows the technician to easily control the needle assembly 10 as he or she applies the substantial forces needed to penetrate the bone. More specifically, the top or proximal surface 38 of the proximal handle member 22 is rounded in conformance with the shape of the palm of the hand. The bottom or distal surface 40 of the distal handle member 24 is also rounded, but is undulating in shape thereby forming finger wells 40A for receiving the technician's fingers. The form of the handle can be other than described herein without departing from the scope of the present invention. The proximal and distal handle members 22, 24 can be connected together in a suitable manner when the stylet 18 is received in the cannula 20, so that the handle 12 acts essentially as a single piece when used to drive the needle 14 through a patient's skin and into the bone. The proximal and distal handle members 22, 24 can be disconnected and moved apart for removing the stylet 18 from the cannula 20.

The cannula safety shield 16 may be moved to cover the distal tip 28 of the cannula 20 after the needle assembly 10 has been used. The safety shield 16 includes a generally tubular housing 50 and an internal locking mechanism (generally indicated at 52 in FIG. 2) capable of releasably locking the tubular housing in position covering the distal tip 28 of the cannula 20. As shown best in FIG. 8, the distal end of the tubular housing 50 includes a funnel-shaped guide 53 leading to an opening 54 directed toward the central axial passageway of the cannula 20. The tubular housing 50 may have any shape that is suitable for hindering access to the sharp tip 28. The tubular housing 50 need not be solid or circular in cross section within the scope of the present invention. The tubular housing 50 and handle 12 may include structure to secure the tubular housing in a retracted position adjacent the handle when not needed. An example of such structure is shown in co-assigned U.S. application Ser. No. 11/146,173, filed Jun. 6, 2005, the disclosure of which is incorporated herein by reference.

Figure 2:
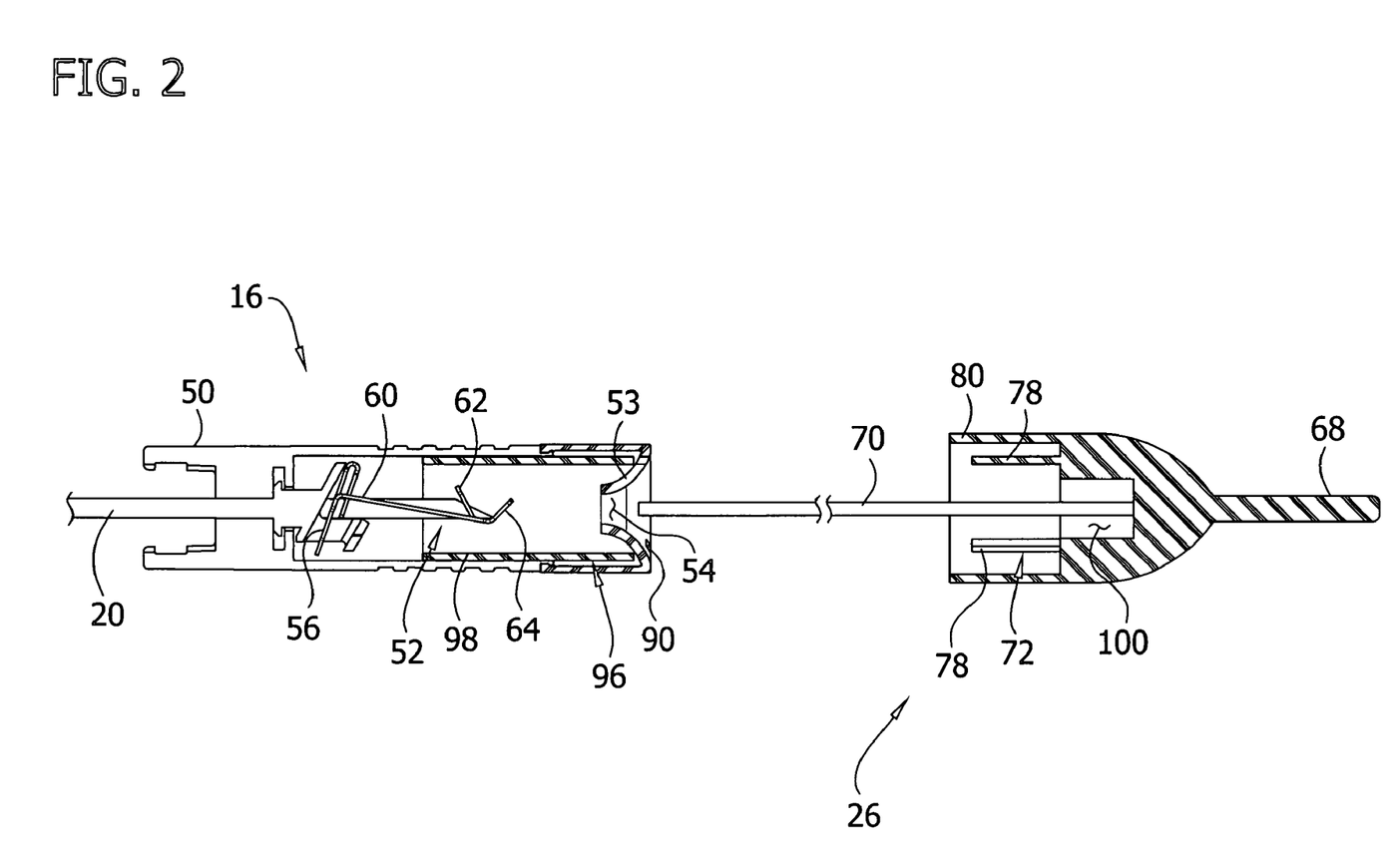
FIG. 2 is a fragmentary partial section of the needle assembly with the obturator entering a safety shield of the needle assembly.

The locking mechanism 52 inside the safety shield 16 comprises a canting member including a base 56 having a hole and a pair of arms 60 (only one is shown) extending generally axially from the base. The arms 60 are connected together by a U-shaped member 62 at their ends and each has an upwardly (as oriented in the figures) bent tab 64 (only one is shown) projecting axially outward from the end. Before the locking mechanism 52 is activated to lock the tubular housing 50 in position, the ends of the arms 60 ride on the exterior surface of the cannula 20. This holds the canting member so that the base 56 is orthogonal so the longitudinal axis of the cannula 20 and the base can move along the cannula (with the safety shield 16), with the cannula sliding unimpeded through the hole in the base. Once the ends of the arms 60 pass the distal tip 28 of the cannula 20, the locking mechanism 52 is weighted so that the ends of the arms move in a generally radial direction toward an opposite side of the longitudinal axis of the needle 14. This causes the base 56 of the canting member to cant relative to the axis of the needle 14 so that the hole in the base is no longer orthogonal to the axis of the cannula. As a result, the base 56 at the edge of the hole grippingly engages the cannula 20 to lock the safety shield 16 in place. It will be understood that a locking mechanism could take on other forms than shown and described without departing from the scope of the present invention. Moreover, a canting member may take on other configurations (e.g., having only a single arm) within the scope of the present invention.

The needle assembly 10 is driven into the bone by grasping the handle 12 and pushing the stylet 18 through the skin, underlying tissue and cortical bone. Once this penetration has been achieved, the stylet 18 is no longer required. The proximal handle member 22 is disconnected from the distal handle member 24 and moved axially away from the distal handle member so that the stylet 18 slides out of the central axial passageway of the cannula 20 while the cannula remains in the bone. In order to collect a sample of bone marrow, the distal handle member is advanced further into the bone. The sharp tip 28 of the cannula 20 cuts into the bone marrow and a sample is received in the central axial passageway of the cannula. The cannula 20 can then be withdrawn from the patient by pulling on the distal handle member 24. The sample remains lodged in the central axial passageway of the cannula 20 near the sharp tip 28. It will be understood that a needle assembly may be used to collect a sample other than of bone marrow within the scope of the present invention.

Figure 4:
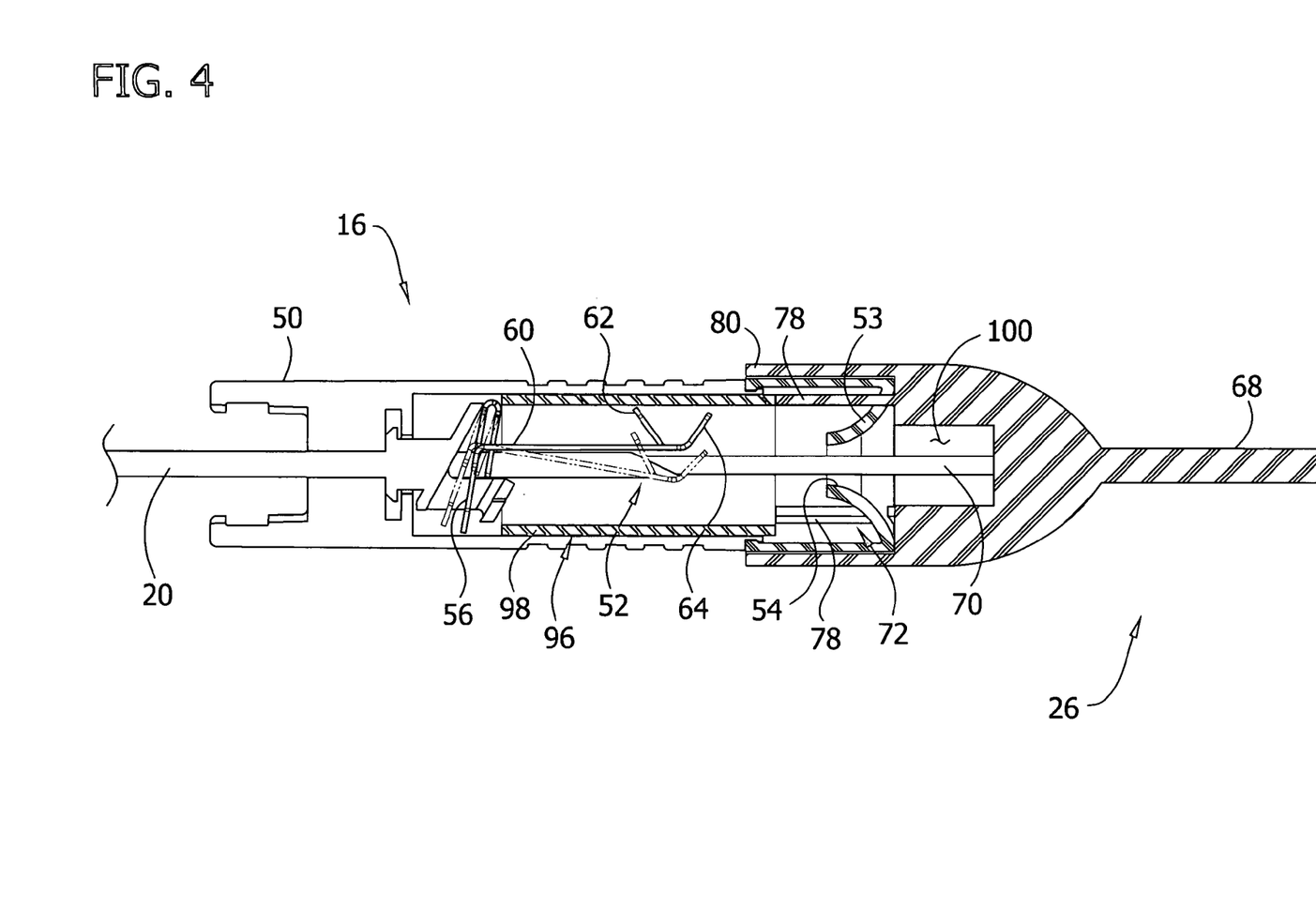
FIG. 4 is the fragmentary elevation of FIG. 2 but showing use of the obturator to reset a locking mechanism of the safety shield.
Figure 6:
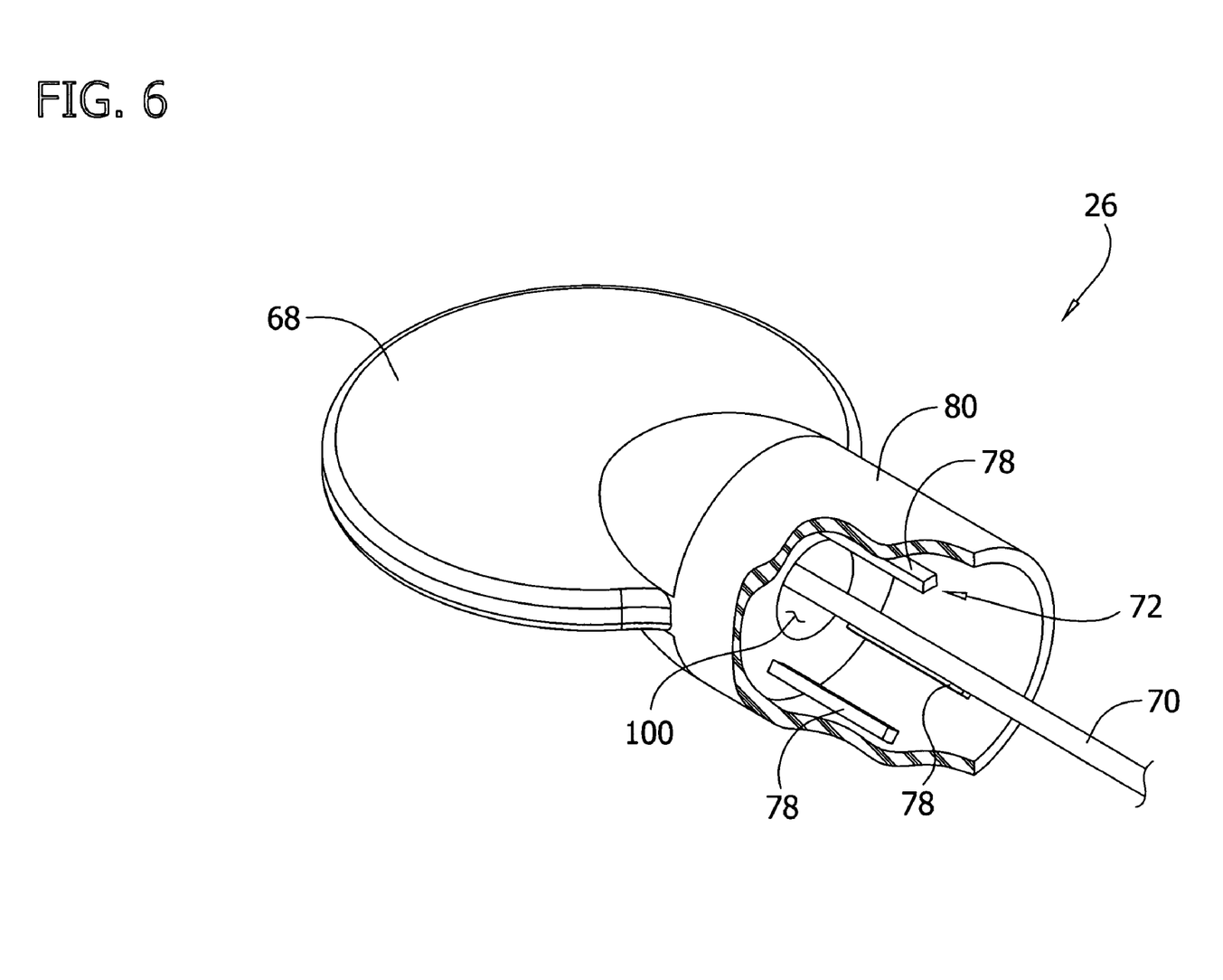
FIG. 6 is a fragmentary perspective of the obturator with parts broken away to show internal construction.
Figure 7:
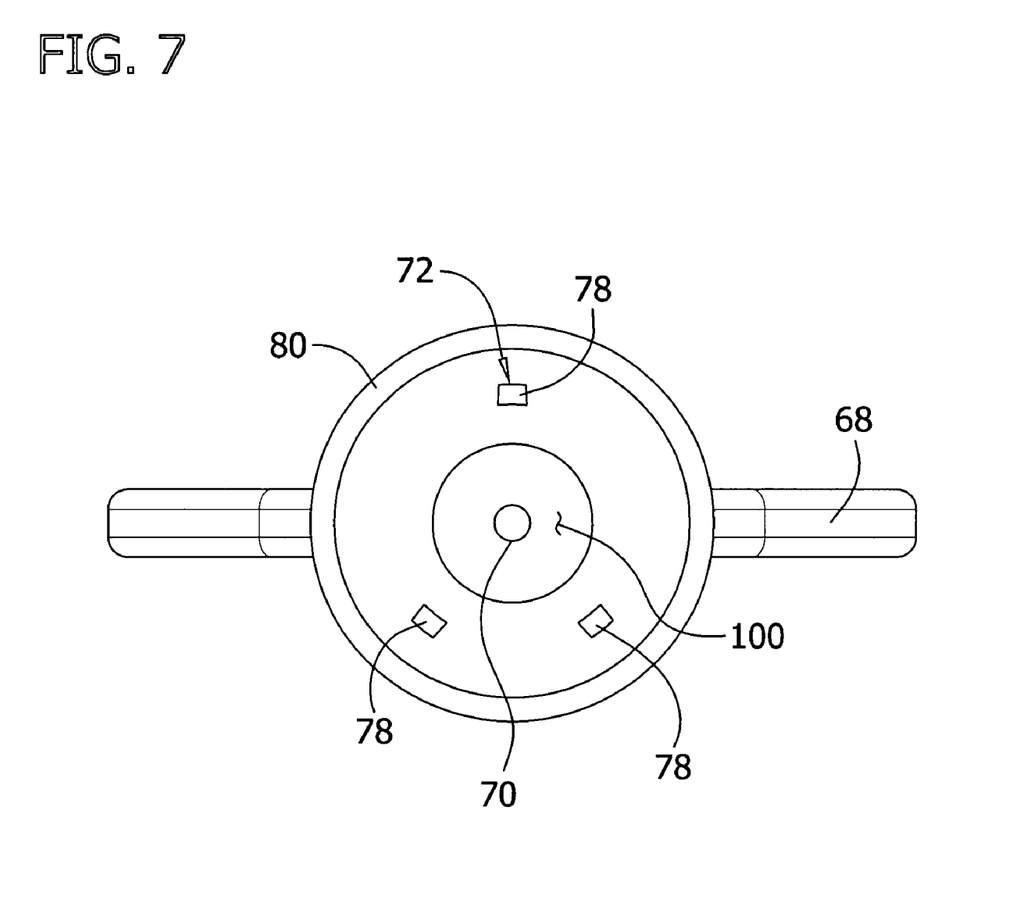
FIG. 7 is an end view of the obturator.

The obturator 26 is used to remove a lodged sample of bone marrow that has been collected in the central axial passageway of cannula 20. The obturator 26 includes a grip 68 and a long, thin shaft 70 extending from the grip that is sized to be received in the central axial passageway of the cannula 20 in generally close fitting relation therein. The grip 68 is sized and shaped to be grasped by a user for manipulating the obturator 26, as will be described. As shown best in FIGS. 6 and 7, a reset member, generally indicated at 72, extends from the grip 68 in the same direction as the shaft 70. In the illustrated embodiment, the reset member 72 comprises projecting portions 78 (e.g., three projecting portions) extending from the grip 68 in the same direction as the shaft 70. The grip 68 further comprises a protective collar 80 extending from the grip 68 to surround the projecting portions 78 and protect the projecting portions from damage. The collar 80 is further adapted to slidably receive the tubular housing 50 in close-fitting relation for proper alignment of the projecting portions 78, as will be discussed in greater detail below with respect to FIG. 4.

Figure 3:
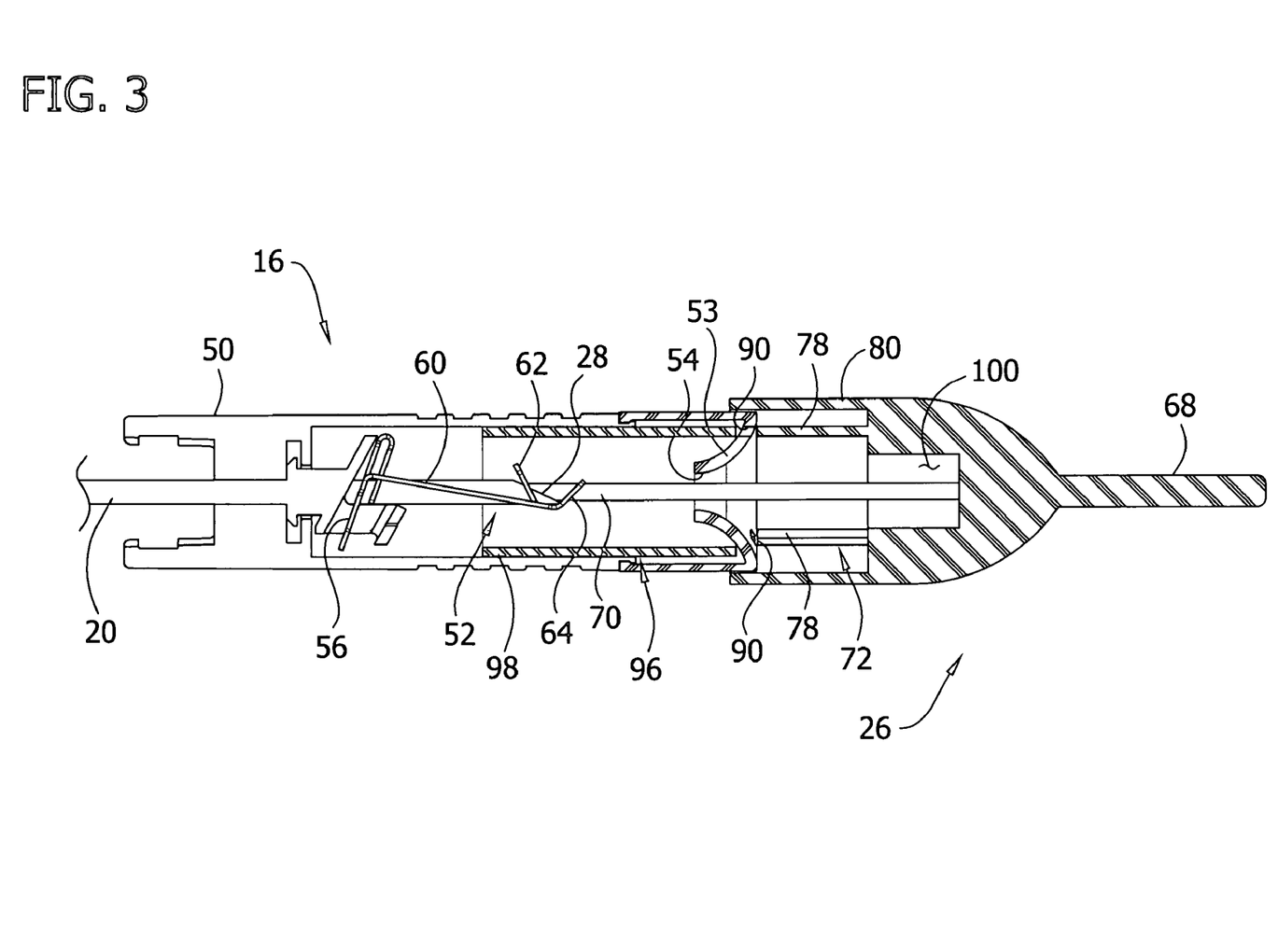
FIG. 3 is the fragmentary elevation of FIG. 2 but showing the obturator inserted to a position in which a sample collected by the needle assembly is pushed out of the needle assembly.

FIG. 2 illustrates an initial position of the obturator 26 with the shaft 70 entering the distal end of the tubular housing 50. The free end of the shaft 70 has not yet entered the central axial passageway of the cannula 20. As shown best in FIG. 8, the distal end of the tubular housing 50 includes the funnel-shaped guide 53 (broadly, "end wall") for guiding the shaft 70 toward the opening 54 in the funnel-shaped guide leading to the central axial passageway of the cannula 20. The grip 68 is pushed to advance the shaft 70 through the funnel-shaped guide 53 and into the central axial passageway, which pushes the sample toward the proximal end of the central axial passageway. Referring to FIG. 3, the shaft 70 is advanced until it protrudes out of the proximal end of the central axial passageway, thereby pushing the sample (not shown) out of the cannula 20 where it can be collected in a Petri dish or other suitable container. As the shaft 70 is advanced, it slides through the funnel-shaped guide 53 at the distal end of the tubular housing 50. The locking mechanism 52 remains engaged so that the safety shield 16 does not move. In the position shown in FIG. 3, free ends of the projecting portions 78 engage the funnel-shaped guide 53. Thus, the technician experiences a resistance to further inward movement of the shaft 70 into the central axial passageway of the cannula 20 because the funnel-shaped guide 53 is restricting movement of the projecting portions 78 of the obturator 26. As would be readily understood by one skilled in the art, the distal end of the tubular housing 50 may be other than funnel-shaped according to the present invention. For example, the distal end may be generally orthogonal to the central axial passageway (or concave or convex) with an opening leading to the central axial passageway of the cannula 20.

The technician may observe the sample ejected from the central axial passageway of the cannula 20. If it is determined that the sample is satisfactory, the obturator 26 can be pulled so that the shaft 70 slides back through and out of the cannula 20. The needle assembly 10 can be discarded, or possibly but less likely, cleaned and sterilized for a subsequent use. If the sample is not satisfactory, however, it will be necessary to obtain a second sample from the same patient. This can be done using the same needle assembly 10, but the tubular housing 50 is locked in place by the locking mechanism 52 over the sharp tip 28 of the cannula 20. The tubular housing 50 needs to be moved away from the tip 28 before the needle assembly 10 can be used to obtain a second sample.

The obturator 26 of the present invention is particularly adapted to permit the tubular housing 50 to be released and moved back from the sharp tip 28 of the cannula 20, without requiring the technician to remove the contaminated obturator from the cannula. This allows the obturator 26 to be used to both eject the sample and reset the safety shield 16 without utilizing an additional resetting device. This is advantageous because the technician can eliminate the extra steps of removing the obturator, locating the resetting device, and inserting the resetting device. Moreover, removing the obturator 26 is undesirable because it is contaminated and its removal may contaminate surrounding surfaces. It should be understood, however, that even with the benefits of an obturator having resetting capabilities, a device other than an obturator 26 incorporating the resetting, or unlocking, features of the obturator described herein, but not functioning as an obturator, is also contemplated as within the scope of the present invention. From the position shown in FIG. 3, the grip 68 can be advanced toward the tubular housing 50 so that the projecting portions 78 are received into a corresponding number of holes 90 (see FIG. 8) in the funnel-shaped guide 53 of the tubular housing. The holes 90 have a generally rectangular shape corresponding to the cross-sectional shape of the projecting portions 78, although other hole shapes are also contemplated as within the scope of the claimed invention. In the example shown, the holes 90 have a different shape than the opening 54 to encourage a user of the device to correctly insert the cylindrical shaft 70 into the opening and the projecting portions 78 into the holes. The grip 68 and projection portions 78 are rotatable together with respect to the tubular housing 50 about a longitudinal axis of the shaft 70, whereby the obturator 26 may be rotated to a particular angular orientation relative to the tubular housing so that the projecting portions precisely align with respective holes 90. Thus, only at this particular angular orientation will the projecting portions 78 be capable of releasing the locking mechanism 52. Guiding structure (not shown) could be provided to guide the projecting portions 78 into the holes 90.

Figure 8:
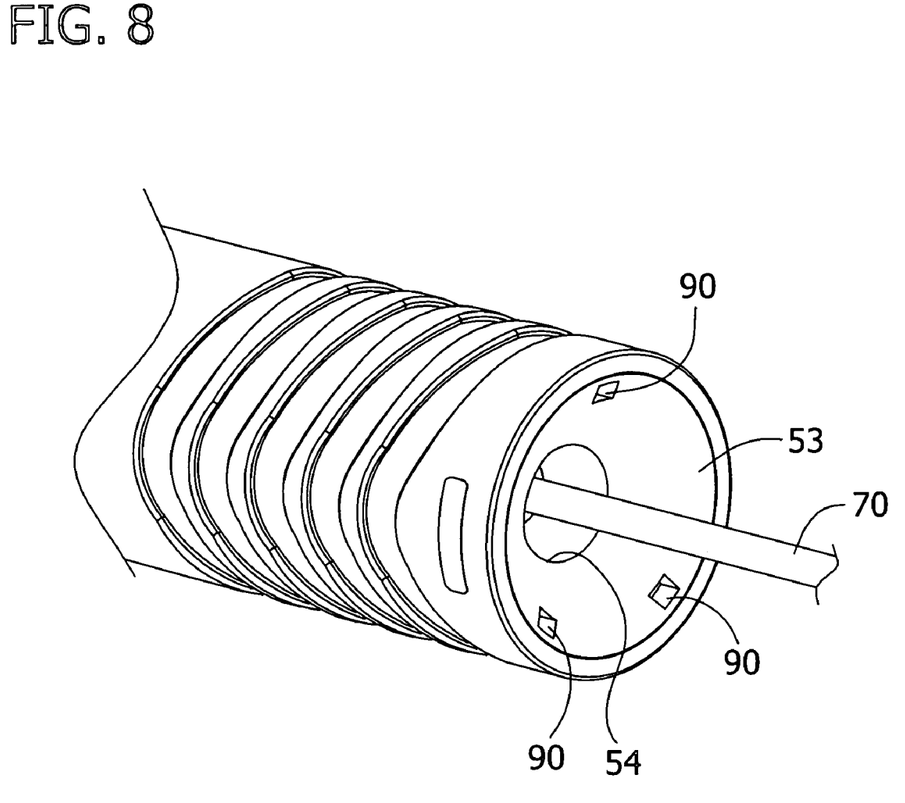
FIG. 8 is a fragmentary perspective of the needle assembly showing the safety shield.

As depicted in the example of FIG. 8, three holes 90 of the tubular housing 50 are arranged in a pattern having a first order rotational symmetry. In other words, the holes 90 of the tubular housing 50 (FIG. 8) and the projecting portions 78 of the obturator 26 (FIGS. 6 and 7) will only fit together in one angular orientation. In another example (not shown), the holes 90 and projection portions 78 may be located at 120 degree intervals relative one another, providing third order rotational symmetry, whereby the holes of the tubular housing 50 and the projecting portions of the obturator 26 may fit together in three distinct angular orientations. Other orders of rotational symmetry (e.g., second, fourth, fifth, etc.) including a fewer or greater number of projection portions 78 and holes 90 are also contemplated as within the scope of the claimed invention. Generally, a higher order of rotational symmetry provides more angular orientations where the holes 90 of the tubular housing 50 and the projecting portions 78 of the obturator 26 will fit together for unlocking the safety shield 16. It should be understood that the cross-sectional areas and shapes of the projecting portions 78 and holes 90 need not be the same, as long as the holes are large enough to receive corresponding projecting portions. Other means for requiring a particular orientation of the obturator 26 with respect to the tubular housing 50 for releasing the locking mechanism 52 are also contemplated as within the scope of the claimed invention (e.g., corresponding collar and tubular housing shapes, mating channels, etc.).

The safety shield 16 further comprises an unlocking mechanism, generally indicated 96, for selective, movable engagement with the locking mechanism 52 for releasing the locking mechanism to permit the tubular housing 50 to move away from the sharp end 28 of the cannula 20. The unlocking mechanism 96 is movable between a first position in which it is free to lock the safety shield 16 in position relative to the sharp end 28 of the cannula 20 and a second position in which the unlocking mechanism releases the locking mechanism 52 to permit movement of the safety shield relative to the sharp end of the cannula. In one example, the unlocking mechanism 96 comprises a generally rigid body such as a cylindrical sleeve 98, or other annular shape, slidably enclosed within and supported by the tubular housing 50 for movement relative to the tubular housing and the locking mechanism 52. In the example shown, the sleeve 98 moves freely within the tubular housing 50, although connections between the sleeve and the tubular housing or the sleeve and the base 56 are also contemplated as within the scope of the invention. Moreover, the sleeve 98 may be biased away from the base 56 to inhibit inadvertent release of the locking mechanism 52. With the projecting portions 78 aligned with the holes 90, the grip 68 can be advanced toward the tubular housing 50 so that the projecting portions 78 pass through the holes 90 and into the tubular housing to engage the sleeve 98 for movement of the sleeve toward the base 56 of the canting member. During advancement of the grip 68, the collar 80 slidably, yet snugly, receives the tubular housing 50 in relatively close engagement to minimize canting of the collar with respect to the tubular housing, thereby facilitating proper alignment of the projecting portions 78 within the holes 90. Moreover, as a leading edge free portion of the sleeve 98 engages the base 56 of the canting member, the sleeve wedges the base of the canting member up to a position in which the base is again substantially orthogonal to the axis of the cannula 20, as shown in phantom in FIG. 4. This positions the hole in the base 56 so that the cannula 20 can slide easily through the canting member. In another example, the sleeve 98 may engage another portion of the canting member (e.g., the bent tab 64) to reset the canting member, without departing from the scope of the claimed invention.

Figure 5:
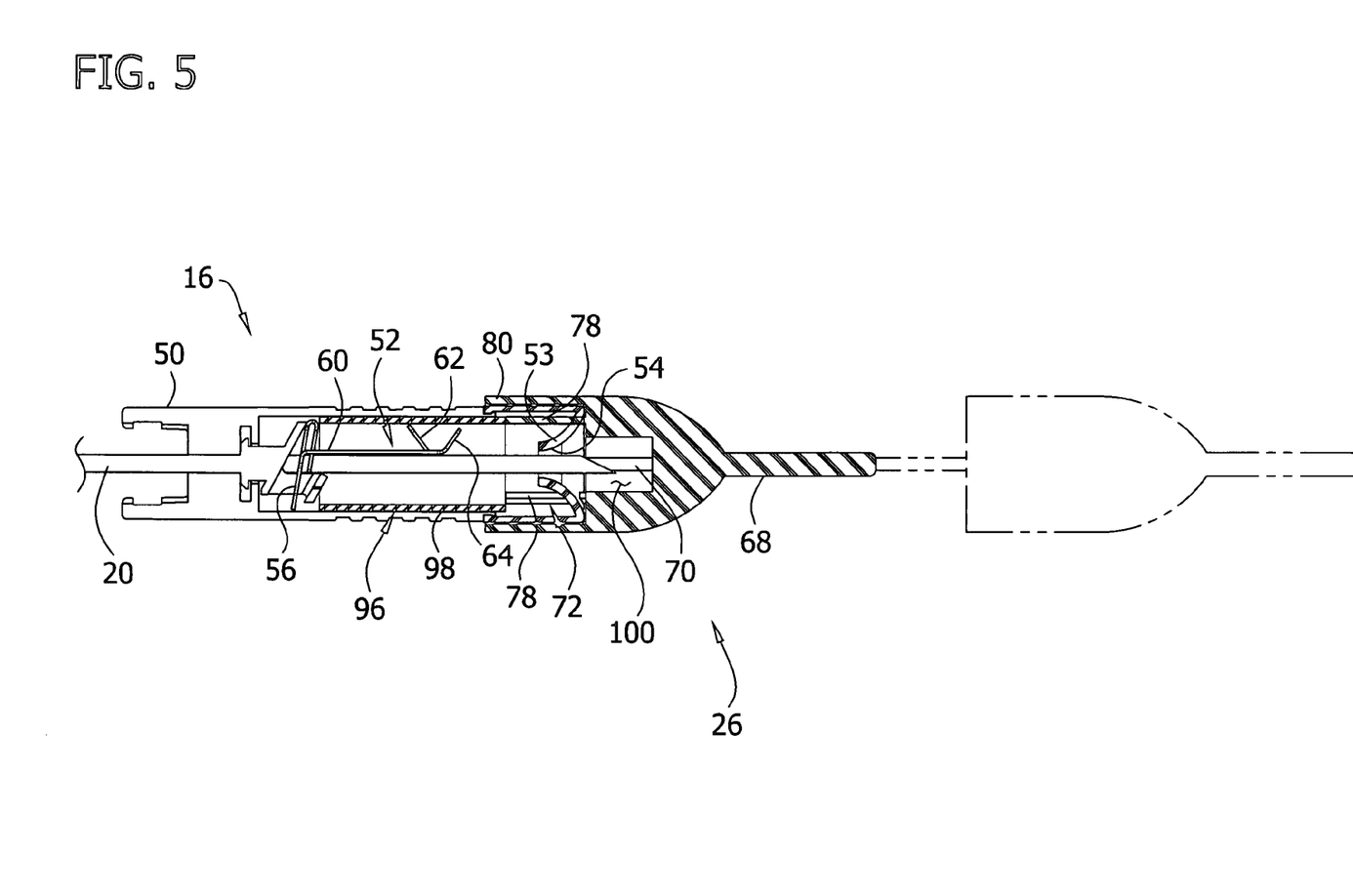
FIG. 5 is the fragmentary elevation of FIG. 2 but showing the safety shield being withdrawn from a sharp end of the needle assembly after release of the locking mechanism.

Thus, as shown in FIG. 5, the tubular housing 50 can be grasped to pull back the safety shield 16 toward the distal housing member 24 so that the sharp tip 28 of the cannula 20 can be exposed. The obturator shaft 70 can be removed, as shown in phantom in FIG. 5, and the stylet 18 can be reinserted into the cannula 20 for a second collection of a sample. It will be appreciated that the arrangement of the projecting portions 78 and holes 90 such that only one angular orientation of the obturator 26 will unlock the locking mechanism 52 inhibits the accidental release of the locking mechanism. The technician must intentionally align the projecting portions 78 and holes 90 to de-activate the locking mechanism 52. In this manner, the funnel-shaped guide 53 acts as a reset inhibitor by only permitting de-activation the locking mechanism 52 with proper alignment of the projecting portions 78 and the holes 90.

As would be readily understood by one skilled in the art, the grip 68 may additionally comprise a cavity 100 opposite the open collar 80 and projecting portions 78 for accommodating the portion of the cannula 20 extending from the distal end of the tubular housing 50 when the projecting portions have fully extended into the holes 90 of the tubular housing.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "up", "down", "top" and "bottom" and variations of these terms is made for convenience, but does not require any particular orientation of the components.

As various changes could be made in the above without departing from the scope of the invention, it is intended that all matter contained in the above description and shown in the accompanying drawings shall be interpreted as illustrative and not in a limiting sense.

What is claimed is:

1. A needle assembly comprising:
   mounting structure;
   a needle mounted on the mounting structure and extending outwardly therefrom, the needle having a longitudinal axis, a sharp end and a central axial passageway;
   a safety shield associated with the needle and comprising a tubular housing adapted for movement relative to the needle between a stowed position in which the tubular housing is spaced from the sharp end of the needle and a deployed position in which the tubular housing covers the sharp end, a locking mechanism adapted to releasably lock the tubular housing in the deployed position covering the sharp end of the needle, and an unlocking mechanism adapted to engage the locking mechanism to unlock the tubular housing from the needle, the unlocking mechanism comprising a generally rigid body disposed in the tubular housing for movement relative to the tubular housing and the locking mechanism; and the locking mechanism comprising a base having an opening receiving the needle therethrough and at least one arm extending outwardly from the base, the rigid body being shaped and arranged for engaging the base of the locking mechanism to release the locking mechanism; and
   an obturator including a shaft sized and shaped for reception in the central axial passageway of the needle, and a reset member operatively connected to the shaft and selectively engageable with the unlocking mechanism of the safety shield for moving the unlocking mechanism into selective engagement with the locking mechanism for releasing the locking mechanism to permit the tubular housing to move away from the sharp end of the needle, wherein the rigid body is generally tubular in shape and receives the needle therein.

2. A needle assembly as set forth in claim 1 wherein the reset member is disposed relative to the shaft so that movement of the obturator in a direction into the central axial passageway can bring the reset member into selective engagement with the tubular body to move the body for releasing the locking mechanism.

3. A needle assembly as set forth in claim 2 wherein the obturator further comprises a grip, the shaft and the reset member extending from the grip in the same direction.

4. A resettable needle safety shield for use in selectively shielding and unshielding a sharp tip of a needle, the safety shield comprising:
   a housing sized and shaped for substantially surrounding the sharp tip of the needle to hinder access to the sharp tip;
   a locking mechanism associated with the housing, the locking mechanism being adapted to lock the housing in position substantially surrounding the sharp needle tip;
   an unlocking mechanism associated with the housing for movement relative to the housing between a first position in which the locking mechanism is free to lock the housing in position relative to the sharp tip of the needle and a second position in which the unlocking mechanism releases the locking mechanism to permit movement of the housing relative to the needle, the unlocking mechanism comprising a generally rigid body disposed in the housing for movement between the first and second positions;

wherein the locking mechanism comprises a base having an opening for receiving the needle therethrough and at least one arm extending outwardly from the base, the rigid body being shaped and arranged for engaging the base of the locking mechanism to release the locking mechanism, wherein the rigid body is generally tubular in shape.

5. A resettable needle safety shield for use in selectively shielding and unshielding a sharp tip of a needle, the safety shield comprising a housing sized and shaped for substantially surrounding the sharp tip of the needle to hinder access to the sharp tip, a locking mechanism associated with the housing, the locking mechanism being adapted to lock the housing in position substantially surrounding the sharp tip of the needle, the housing including an end wall having at least one hole therein arranged in relation to the locking mechanism for receiving structure through the end wall for use in releasing the locking mechanism;

wherein the housing further comprises a plurality of holes in the end wall, the holes being arranged for receiving said structure through the end wall in one predetermined orientation of the structure, the structure comprising a reset member including projecting portions having a non-round cross sectional shape, the holes in the end wall each having a shape that is substantially the same as the cross sectional shape of each of the projecting portions.

6. A needle safety shield as set forth in claim 5 further comprising an unlocking mechanism supported by the housing for movement therein between a first position in which the locking mechanism is free to lock the housing in position relative to the sharp needle tip and a second position in which the unlocking mechanism releases the locking mechanism to permit movement of the housing relative to the needle.

* * * * *